United States Patent
Olson et al.

(10) Patent No.: US 12,098,201 B2
(45) Date of Patent: *Sep. 24, 2024

(54) ANTI-TIM3 MONOCLONAL ANTIBODIES AND CHIMERIC ANTIGEN RECEPTORS

(71) Applicant: NantBio, Inc., Culver City, CA (US)

(72) Inventors: Clifford Anders Olson, Culver City, CA (US); Kayvan Niazi, Culver City, CA (US); Hermes J. Garban, Culver City, CA (US); Raymond Wong, Los Angeles, CA (US); Shiho Tanaka, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/302,724

(22) Filed: Apr. 18, 2023

(65) Prior Publication Data

US 2023/0287113 A1 Sep. 14, 2023

Related U.S. Application Data

(63) Continuation of application No. 17/587,546, filed on Jan. 28, 2022, now Pat. No. 11,753,467.

(60) Provisional application No. 63/142,777, filed on Jan. 28, 2021.

(51) Int. Cl.
| | |
|---|---|
| *C07K 16/28* | (2006.01) |
| *A61K 47/68* | (2017.01) |
| *C07K 14/54* | (2006.01) |
| *C07K 14/715* | (2006.01) |
| *C07K 14/725* | (2006.01) |

(52) U.S. Cl.
CPC ...... *C07K 16/2803* (2013.01); *A61K 47/6849* (2017.08); *C07K 14/5443* (2013.01); *C07K 14/7051* (2013.01); *C07K 14/7155* (2013.01); *C07K 2317/56* (2013.01); *C07K 2319/30* (2013.01)

(58) Field of Classification Search
CPC ............ C07K 16/2803; C07K 14/5443; C07K 14/7051; C07K 14/7155; C07K 2317/56; C07K 2319/30; A61K 47/6849
See application file for complete search history.

(56) References Cited

U.S. PATENT DOCUMENTS

| | | | |
|---|---|---|---|
| 11,753,467 B2 * | 9/2023 | Olson | C07K 14/7051 424/178.1 |
| 11,884,725 B2 | 1/2024 | Li et al. | |
| 2019/0374579 A1 | 12/2019 | Davila | |
| 2022/0089720 A1 | 3/2022 | Schebye et al. | |

FOREIGN PATENT DOCUMENTS

| | | | |
|---|---|---|---|
| CN | 111886023 A | 11/2020 | |
| CN | 111886255 A | 11/2020 | |
| EP | 3 585 403 A1 | 1/2020 | |
| WO | 2016/068803 A1 | 5/2016 | |
| WO | WO-2016149665 A1 * | 9/2016 | ............ A61K 35/17 |
| WO | 2016/144803 A8 | 11/2016 | |
| WO | 2017/205721 A1 | 11/2017 | |
| WO | 2018/156434 A1 | 8/2018 | |
| WO | 2019/140229 A1 | 7/2019 | |
| WO | 2019/143607 A1 | 7/2019 | |

OTHER PUBLICATIONS

Ngiow et al., "Anti-TIM3 Antibody Promotes T Cell IFN-g-Mediated Antitumor Immunity and Suppresses Established Tumors", Cancer Research, Microenvironment and Immunology, vol. 71, No. 10, May 15, 2011, pp. 3540-3551.
Ngiow et al., "Prospects for TIM3-Targeted Antitumor Immunotherapy", Cancer Research, Review, vol. 71, No. 21, Nov. 1, 2011, pp. 6567-6571.
Extended European Search Report received for EP Patent Application Serial No. 22152774.0 dated Oct. 6, 2022, 9 pages.
Hosseinkhani et al., "Immune Checkpoints and CAR-T Cells: The Pioneers in Future Cancer Therapies?", International Journal of Molecular Sciences, vol. 21, No. 21, Article 8305, Nov. 5, 2020, pp. 1-26.
He et al., "Bispecific and split CAR T cells targeting CD13 and TIM3 eradicate acute myeloid leukemia", Blood vol. 135, No. 10, Mar. 5, 2020, pp. 713-723.
Qin et al., "Novel immune checkpoint targets: moving beyond PD-1 and CTLA-4", Molecular, vol. 18, No. 1, Nov. 6, 2019, pp. 1-14.
First Office Action received for CN Application No. 202210105428.7 dated Dec. 29, 2023, 17 pages (including English Translation).

* cited by examiner

*Primary Examiner* — Adam Weidner
*Assistant Examiner* — Laura Ann Essex
(74) *Attorney, Agent, or Firm* — Martin Fessenmaier; Umberg Zipser LLP

(57) ABSTRACT

Antibodies, fragments thereof, and chimeric proteins comprising the same are presented that have specific binding activity against T-cell immunoglobulin mucin receptor 3 (TIM3). Advantageously, contemplated molecules can be used in pharmaceutical compositions for immune therapy, particularly in individuals receiving cancer vaccines and/or checkpoint inhibitor treatment.

19 Claims, No Drawings

Specification includes a Sequence Listing.

ANTI-TIM3 MONOCLONAL ANTIBODIES AND CHIMERIC ANTIGEN RECEPTORS

This application is a continuation application of allowed US application with the Ser. No. 17/587,546, which was filed Jan. 28, 2022, and which claims priority to our U.S. Provisional Patent application with the Ser. No. 63/142,777, which was filed Jan. 28, 2021, both of which is incorporated by reference in their entirety.

SEQUENCE LISTING

The content of the XML file of the sequence listing named 102719.0033US2.xml, which is 79 KB in size, created on Apr. 12, 2023 and which is electronically submitted via Patent Center along with the present application is incorporated by reference in its entirety.

FIELD OF THE INVENTION

The field of the invention is target specific binding molecules, especially as it relates to antibodies and chimeric antigen receptors, and derivatives thereof with binding specificity against T-cell immunoglobulin mucin receptor 3 (TIM3).

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The T-cell immunoglobulin mucin receptor 3 (TIM3) is a cell surface receptor that is implicated in modulating innate and adaptive immune responses and is generally known to exert inhibiting functions. However, some reports have also suggested stimulating functions, which may be influenced by the cellular context and/or the respective ligand. Most typically, TIM3 regulates macrophage activation, inhibits T-helper type 1 lymphocyte (Th1)-mediated auto- and alloimmune responses, and promotes immunological tolerance. TIM3 function is also strongly influenced by the type of cell in which it is expressed. For example, in CD8+ cells, TIM3 attenuates TCR-induced signaling, specifically by blocking NF-kappaB and NFAT promoter activities, resulting in the loss of IL-2 secretion. Expressed on Treg cells, TIM3 can inhibit Th17 cell responses. Expressed on dendritic cells (DCs), TIM3 positively regulates innate immune response and in synergy with Toll-like receptors promotes secretion of TNF-alpha. On the other hand, in tumor-infiltrating DCs, TIM3 suppresses nucleic acid-mediated innate immune response by interaction with HMGB1 and interfering with nucleic acid-sensing and trafficking of nucleic acids to endosomes.

Increasing recognition of the role of TIM3 lead to the development of various TIM3 targeting molecules. For example, WO 2019/140229 and WO 2016/144803 teach specific anti-TIM3 antibodies, and selected treatment methods using anti-TIM3 antibodies are described in WO2019143607A1. In other examples, as described in EP 3585403, chimeric antigen receptor (CAR) polypeptides were expressed in immune effector cells, such as T cells or Natural Killer (NK) cells and used in adoptive cell transfer to target and kill TIM3-expressing cancers. Further studies reported that anti-TIM3 antibodies promoted T cell IFN-γ-mediated antitumor immunity and suppressed established tumors as is discussed in Cancer Res. 2011 May 15; 71(10): 3540-51; doi: 10.1158/0008-5472, and prospects for TIM3-targeted antitumor immunotherapy are discussed in Cancer Res. 2011 Nov. 1; 71(21):6567-71. doi: 10.1158/0008-547. While such compositions and methods advantageously open at least some TIM3-specific therapeutic approaches, the number and avidity of TIM3 binder is relatively limited.

Thus, even though various systems and methods of TIM3 targeting are known in the art, all or almost all of them suffer from several drawbacks. Therefore, there remains a need for compositions and methods for new and improved TIM3 specific therapeutic and diagnostic molecules.

SUMMARY OF THE INVENTION

The inventive subject matter is directed to various compositions and methods of TIM3 specific therapeutic and diagnostic molecules and their use in diagnosis and treatment of an individual.

In one aspect of the inventive subject matter, the inventors contemplate an isolated antibody or fragment thereof, wherein the antibody or fragment thereof binds to T-cell immunoglobulin mucin receptor 3 (TIM3) and includes a variable heavy chain (VH) domain and a variable light chain (VL) domain, wherein the VH domain is selected form the group consisting of SEQ ID NO:1, SEQ ID NO:3, SEQ ID NO:5, SEQ ID NO:7, SEQ ID NO:9, and SEQ ID NO:11, and wherein the VL domain is selected form the group consisting of SEQ ID NO:2, SEQ ID NO:4, SEQ ID NO:6, SEQ ID NO:8, SEQ ID NO:10, and SEQ ID NO:12.

In one embodiment, the antibody or fragment comprises VH64-6 (SEQ ID NO:1) and VL64-6 (SEQ ID NO:2), optionally coupled together by a linker to form an scFv. In another embodiment, the antibody or fragment comprises VH64-15 (SEQ ID NO:3) and VL64-15 (SEQ ID NO:4), optionally coupled together by a linker to form an scFv. In a further embodiment, the antibody or fragment comprises VH64-31 (SEQ ID NO:5) and VL64-31 (SEQ ID NO:6), optionally coupled together by a linker to form an scFv. In a still further embodiment, the antibody or fragment comprises VH64-32 (SEQ ID NO:7) and VL64-32 (SEQ ID NO:8), optionally coupled together by a linker to form an scFv. In yet another embodiment, the antibody or fragment comprises VH64-39 (SEQ ID NO:9) and VL64-39 (SEQ ID NO:10), optionally coupled together by a linker to form an scFv. In a further embodiment, antibody or fragment comprises VH66-6 (SEQ ID NO:11) and VL66-6 (SEQ ID NO:12), optionally coupled together by a linker to form an scFv.

Most typically, but not necessarily, antibody is an IgG1 antibody or an scFv, and/or may further include a therapeutic agent (e.g., a chemotherapeutic drug, a radionuclide, or an immune stimulant such as a cytokine, a cytokine analog, a chemokine, or a checkpoint inhibitor). Alternatively, or additionally, the antibody or fragment may also comprise a detectable label.

In other embodiments, the inventors also contemplate a chimeric protein that comprises the antibody or fragment presented herein. For example, the chimeric protein may form a chimeric antigen receptor (CAR), which may have a CD3zeta (CD3ζ) or Fc receptor epsilon (FcεRIγ) signaling domain, or that may have one or more of a CD28 signaling domain, a 4-1BB signaling domain, and a CD3zeta (CD3ζ) signaling domain. Most typically, the CAR may have a CD8 hinge domain and a CD28 transmembrane domain. As will be readily appreciated, the CAR will be a recombinant CAR that is expressed in and presented on the surface of an NK cell or a cytotoxic T cell. In other examples, the chimeric protein may form a bispecific fusion protein (e.g., comprising an IgG Fc portion, and optionally further comprising at least one of an IL15a receptor portion, an IL15 portion, and an IL15 superagonist portion) or may form a bispecific killer cell engager (BiKE) or a trispecific killer cell engager (TriKe).

Therefore, the inventors also contemplate a recombinant nucleic acid that encodes the isolated antibody or fragment, or the chimeric protein presented herein. For example, the nucleic acid may be part of an expression vector or part of a recombinant viral genome or may be in form of a linear DNA. On the other hand, the recombinant nucleic acid may also be an RNA.

Viewed from a different perspective, the inventors also contemplate a pharmaceutical composition that includes a pharmaceutically acceptable carrier in combination with the isolated antibody or fragment or the chimeric protein as presented herein. Similarly, the inventors also contemplate a pharmaceutical composition that includes a pharmaceutically acceptable carrier in combination with the recombinant nucleic acid as presented herein.

In another aspect of the inventive subject matter, the inventors also a method of treating an individual, in which the pharmaceutical compositions presented herein are administered to the individual, typically to thereby reduce immune suppression in the individual. Most typically, the individual is being treated with a cancer vaccine and/or a checkpoint inhibitor. Therefore, the inventors also contemplate the use of the pharmaceutical compositions as presented herein in the treatment of cancer in an individual.

Various objects, features, aspects and advantages of the inventive subject matter will become more apparent from the following detailed description of preferred embodiments.

DETAILED DESCRIPTION

The inventors have discovered various anti-TIM3 antibodies that have high affinity and specificity with respect to binding to TIM3. In particularly preferred aspects, contemplated antibodies are human IgG$_1$ antibodies that have the VH and VL domains as shown below. However, it should be appreciated that the sequences presented herein can vary to at least some degree and may therefore have one or more amino acid substitutions, insertions, and/or deletions as is discussed in more detail below. Most typically, but not necessarily, $V_H$ and $V_L$ domains, or heavy and light chains with the same preceding numeral (e.g., 64-6) will be present in a TIM3 binding construct. However, other TIM3 binding constructs may only have the $V_H$ or $V_L$ domain, or a $V_H$ and a $V_L$ domain with non-identical preceding numeral. Moreover, TIM3 binding constructs may include those that have at least some of the CDRs (e.g., at least those from $V_H$ domain) as listed below.

64-6 $V_H$ domain amino acid sequence:
(SEQ ID NO: 1)
EVQLVESGGGLVQPGGSLRLSCAASGFTFSRYAMHWVRQAPGKGLEWVSAI
SGSGGYTYYADSVKGRFTISRDNSKNTLYLQMNSLRAEDTAVYYCARDRHW
VLSAFDVWGQGTLVTVSS 64-6 $V_L$ domain amino acid sequence:
(SEQ ID NO: 2)
DIQMTQSPSSLSASVGDRVTITCQASQDISNYLNWYQQKPGKAPKLLIYDA
SNLETGVPSRFSGSGSGTDFTFTISSLQPEDIATYYCQQYDTFPFTFGQGT
KVEIK 64-15 $V_H$ domain amino acid sequence:
(SEQ ID NO: 3)
EVQLVESGGGLVQPGGSLRLSCAASGFTFSSYYMHWVRQAPGKGLEWVSGI
SGSGGSTYYADSVKGRFTISRDNSKNTLYLQMNSLRAEDTAVYYCARGRGA
WPFTRVVAFDVWGQGTLVTVSS 64-15 $V_L$ domain amino acid sequence:
(SEQ ID NO: 4)
DIQMTQSPSSLSASVGDRVTITCQASQDISNYLNWYQQKPGKAPKLLIYDA
SNLETGVPSRFSGSGSGTDFTFTISSLQPEDIATYYCQQWTALPLTFGQGT
KVEIK 64-31 $V_H$ domain amino acid sequence:
(SEQ ID NO: 5)
MEVQLVESGGGLVQPGGSLRLSCAASGFTFSAYAMHWVRQAPGKGLEWVSA
INGNGGRTYYADSVKGRFTISRDNSKNTLYLQMNSLRAEDTAVYYCARDLT
RTVPFAFDVWGQGTLVTVSS 64-31 $V_L$ domain amino acid sequence:
(SEQ ID NO: 6)
DIQMTQSPSSLSASVGDRVTITCQASQDISNYLNWYQQKPGKAPKLLIYDA
SNLETGVPSRFSGSGSGTDFTFTISSLQPEDIATYYCQQATGWPFTFGQGT
KVEIK 64-32 $V_H$ domain amino acid sequence:
(SEQ ID NO: 7)
MEVQLVESGGGLVQPGGSLRLSCAASGFTFSKYAMHWVRQAPGKGLEWVSA
ISGSGGYTYYADSVKGRFTISRDNSKNTLYLQMNSLRAEDTAVYYCARDLD
FRIVGFDVWGQGTLVTVSS 64-32 $V_L$ domain amino acid sequence:
(SEQ ID NO: 8)
DIQMTQSPSSLSASVGDRVTITCQASQDISNYLNWYQQKPGKAPKLLIYDA
SNLETGVPSRFSGSGSGTDFTFTISSLQPEDIATYYCQQFNTVPLTFGQGT
KVEIK 64-39 $V_H$ domain amino acid sequence:
(SEQ ID NO: 9)
MEVQLVESGGGLVQPGGSLRLSCAASGFTFSRYAMHWVRQAPGKGLEWVSG
ISGSGGGTYYADSVKGRFTISRDNSKNTLYLQMNSLRAEDTAVYYCARDLD
YRVSGFDVWGQGTLVTVSS 64-39 $V_L$ domain amino acid sequence:
(SEQ ID NO: 10)
DIQMTQSPSSLSASVGDRVTITCQASQDISNYLNWYQQKPGKAPKLLIYDA
SNLETGVPSRFSGSGSGTDFTFTISSLQPEDIATYYCQQFYSVPLTFGQGT
KVEIK 66-6 V_H domain amino acid sequence:
(SEQ ID NO: 11)
MEVQLVESGGGLVQPGGSLRLSCAASGFTFSKYAMHWVRQAPGKGLEWVSA

ISGSGGSTYYADSVKGRFTISRDNSKNTLYLQMNSLRAEDTAVYYCARDLD

YRFSGFDVWGQGTLVTVSS 66-6 V_L domain amino acid sequence:
(SEQ ID NO: 12)
DIQMTQSPSSLSASVGDRVTITCQASQDISNYLNWYQQKPGKAPKLLIYDA

SNLETGVPSRFSGSGSGTDFTFTISSLQPEDIATYYCQQFAAIPLTFGQGT

KVEIK

As will be readily appreciated, the binding specificity of the V_H and V_L domains is dictated by their respective CDR regions, and Table 1 below shows the amino acid sequences for the CDRs in the V_H and V_L domains. Therefore, based on the known CDR sequences, it is contemplated that antibodies and fragments thereof can be prepared that bind TIM3 and that include at least some of the CDRs of SEQ ID Nos: 25-60.

TABLE 1

| Clone | CDR-H1 | CDRH-2 | CDR-H3 | CDR-L1 | CDR-L2 | CDR-L3 |
|---|---|---|---|---|---|---|
| 64-6 | SRYAMH SEQ ID NO: 25 | AISGSGGYTY SEQ ID NO: 26 | DRHWVLSAFDV SEQ ID NO: 27 | QASQDISNYLN SEQ ID NO: 28 | DASNLET SEQ ID NO: 29 | QQYDTFPFT SEQ ID NO: 30 |
| 64-15 | SSYYMH SEQ ID NO: 31 | GISGSGGSTY SEQ ID NO: 32 | CARGRGAWPFT RVVAFDV SEQ ID NO: 33 | QASQDISNYLN SEQ ID NO: 34 | DASNLET SEQ ID NO: 35 | QQWTALPLT SEQ ID NO: 36 |
| 64-31 | SAYAMH SEQ ID NO: 37 | AINGNGGRTY SEQ ID NO: 38 | DLTRTVPFAFDV SEQ ID NO: 39 | QASQDISNYLN SEQ ID NO: 40 | DASNLET SEQ ID NO: 41 | QQATGWPFT SEQ ID NO: 42 |
| 64-32 | SKYAMH SEQ ID NO: 43 | AISGSGGYTY SEQ ID NO: 44 | DLDFRIVGFDV SEQ ID NO: 45 | QASQDISNYLN SEQ ID NO: 46 | DASNLET SEQ ID NO: 47 | QQFNTVPLT SEQ ID NO: 48 |
| 64-39 | SRYAMH SEQ ID NO: 49 | GISGSGGGTY SEQ ID NO: 50 | DLDYRVSGFDV SEQ ID NO: 51 | QASQDISNYLN SEQ ID NO: 52 | DASNLET SEQ ID NO: 53 | QQFYSVPLT SEQ ID NO: 54 |
| 66-6 | SKYAMH SEQ ID NO: 55 | AISGSGGSTY SEQ ID NO: 56 | DLDYRFSGFDV SEQ ID NO: 57 | QASQDISNYLN SEQ ID NO: 58 | DASNLET SEQ ID NO: 59 | QQFAAIPLT SEQ ID NO: 60 |

For example, using the CDRs and V_H and V_L domain information above, IgG_1 antibodies can be prepared having the following exemplary heavy chains (HC) and light chain (LC) sequences with amino acid sequences of SEQ ID Nos:13-24. Most typically, but not necessarily, HC and LC with the same preceding numeral (e.g., 64-6) will be present in a TIM3 binding antibody. However, other TIM3 binding antibodies may have a heavy chain and a light chain with non-identical preceding numeral.

64-6 HC amino acid sequence:
(SEQ ID NO: 13)
EVQLVESGGGLVQPGGSLRLSCAASGFTFSRYAMHWVRQAPGKGLEWVSAI

SGSGGYTYYADSVKGRFTISRDNSKNTLYLQMNSLRAEDTAVYYCARDRHW

VLSAFDVWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFF

LYSKLTVDKSRWQQGNVFSCSVMHEALHNHYTQKSLSLSPGK 64-6 LC amino acid sequence:
(SEQ ID NO: 14)
DIQMTQSPSSLSASVGDRVTITCQASQDISNYLNWYQQKPGKAPKLLIYDA

SNLETGVPSRFSGSGSGTDFTFTISSLQPEDIATYYCQQYDTFPFTFGQGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC 64-15 HC amino acid sequence:
(SEQ ID NO: 15)
EVQLVESGGGLVQPGGSLRLSCAASGFTFSSYYMHWVRQAPGKGLEWVSGI

SGSGGSTYYADSVKGRFTISRDNSKNTLYLQMNSLRAEDTAVYYCARGRGA

WPFTRVVAFDVWGQGTLVTVSSASTKGPSVFPLAPSSKSTSGGTAALGCLV

KDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK 64-15 LC amino acid sequence:
(SEQ ID NO: 16)
DIQMTQSPSSLSASVGDRVTITCQASQDISNYLNWYQQKPGKAPKLLIYDA
SNLETGVPSRFSGSGSGTDFTFTISSLQPEDIATYYCQQWTALPLTFGQGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC 64-31 HC amino acid sequence:
(SEQ ID NO: 17)
MEVQLVESGGGLVQPGGSLRLSCAASGFTFSAYAMHWVRQAPGKGLEWVSA
INGNGGRTYYADSVKGRFTISRDNSKNTLYLQMNSLRAEDTAVYYCARDLT
RTVPFAFDVWGQGTLVTVSSASTKGPSVFPLAPSSKSTSGGTAALGCLVKD
YFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDGS
FFLYSKLTVDKSRWQQGNVFSCSVMHEALHNHYTQKSLSLSPGK 64-31 LC amino acid sequence:
(SEQ ID NO: 18)
DIQMTQSPSSLSASVGDRVTITCQASQDISNYLNWYQQKPGKAPKLLIYDA
SNLETGVPSRFSGSGSGTDFTFTISSLQPEDIATYYCQQATGWPFTFGQGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC 64-32 HC amino acid sequence:
(SEQ ID NO: 19)
MEVQLVESGGGLVQPGGSLRLSCAASGFTFSKYAMHWVRQAPGKGLEWVSA
ISGSGGYTYYADSVKGRFTISRDNSKNTLYLQMNSLRAEDTAVYYCARDLD
FRIVGFDVWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK 64-32 LC amino acid sequence:
(SEQ ID NO: 20)
DIQMTQSPSSLSASVGDRVTITCQASQDISNYLNWYQQKPGKAPKLLIYDA
SNLETGVPSRFSGSGSGTDFTFTISSLQPEDIATYYCQQFNTVPLTFGQGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC 64-39 HC amino acid sequence:
(SEQ ID NO: 21)
MEVQLVESGGGLVQPGGSLRLSCAASGFTFSRYAMHWVRQAPGKGLEWVSG
ISGSGGGTYYADSVKGRFTISRDNSKNTLYLQMNSLRAEDTAVYYCARDLD
YRVSGFDVWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK 64-39 LC amino acid sequence:
(SEQ ID NO: 22)
DIQMTQSPSSLSASVGDRVTITCQASQDISNYLNWYQQKPGKAPKLLIYDA
SNLETGVPSRFSGSGSGTDFTFTISSLQPEDIATYYCQQFYSVPLTFGQGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC 66-6 HC amino acid sequence:
(SEQ ID NO: 23)
MEVQLVESGGGLVQPGGSLRLSCAASGFTFSKYAMHWVRQAPGKGLEWVSA
ISGSGGSTYYADSVKGRFTISRDNSKNTLYLQMNSLRAEDTAVYYCARDLD
YRFSGFDVWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK 66-6 LC amino acid sequence:
(SEQ ID NO: 24)
DIQMTQSPSSLSASVGDRVTITCQASQDISNYLNWYQQKPGKAPKLLIYDA
SNLETGVPSRFSGSGSGTDFTFTISSLQPEDIATYYCQQFAAIPLTFGQGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC In one typical example, the inventors prepared antibodies using the above HC and LC sequences with matching preceding numbers and tested the so prepared antibodies for TIM3 binding. Table 2 depicts exemplary results for determination of dissociation constants of the antibodies. More specifically, $K_D$ determination was done by SPR (Pioneer FE) or Octet (Red96e) at 25° C. or 37° C. All values are ×10$^{-9}$M. anti-TIM-3 IgG1 antibodies were captured on the chip surface using anti-human Fc antibody (SPR) or AHC sensor (Octet), and human TIM-3 was the analyte.

TABLE 2

| aTIM-3 IgG1 | 25° C. | 37° C. |
|---|---|---|
| 64-6 | 0.46 | 2.50 |
| 64-15 | 0.71 | 5.40 |
| 64-31 | 10.4 | 36.5 |
| 64-32 | 0.39 | 0.92 |
| 64-39 | 1.53 | 6.39 |
| 66-6 | 1.69 | 7.01 |

Notably, despite being the same type of antibody (here: $IgG_1$) with otherwise identical framework regions, the tested antibodies exhibited unexpected affinity differences spanning almost three orders of magnitude as can be seen from Table 2 above. Here, antibodies 64-6, 64-15, and 64-32 had sub-nanomolar $K_D$ values at 25° C., while antibodies 64-39 and 66-6 had single-digit $K_D$ values at 25° C., and antibody 64-31 had a double-digit $K_D$ value at 25° C. Similarly, the $K_D$ differences between 25° C. and 37° C. for each antibody were unexpectedly low for antibodies 64-32 and 64-31 (2.36× and 3.51) whereas antibodies 64-6, 64-39, and 66-6 were higher (5.43×, 4.18×, 4.15×), and antibody 64-15 was even higher (7.61×). Viewed from a different perspective, antibodies 64-6 and 64-32 had an affinity to TIM-3 at physiological temperatures that was two orders of magnitude stronger than antibody 64-31.

Of course, it should be appreciated that the inventive subject matter is not limited to the exact sequences noted above, but one or more of the sequences may include one or more amino acid changes. Most preferably, the changes will not result in a substantial reduction of specificity and/or affinity. Thus, contemplated amino acid changes will typically be in the framework regions of the $V_H$ and/or $V_L$ domains, and/or in the constant regions of HC and/or LC. Viewed from a different perspective, amino acid changes will preferably not be present in the CDR region. For example, contemplated sequences will have between 98-99% identity or homology, or between 96-98% identity or homology, or between 92-96% identity or homology, or between 85-92% identity or homology, or between 75-85% identity or homology, most typically (but not necessarily) with the changed amino acids outside the CDRs. Among other options for amino acid changes, one or more amino acids can be changed to 'humanize' a non-human antibody, and/or to move or eliminate one or more glycosylation sites.

Moreover, it should be noted that contemplated antibodies will expressly include various forms such as monoclonal antibodies, multi-specific antibodies, human antibodies, humanized antibodies, synthetic antibodies, chimeric antibodies, single domain antibodies, single-chain Fvs (scFv), single chain antibodies, disulfide-linked Fvs (sdFv), BiKes, and TriKes as is described in more detail below. Of course, it should also be noted that the term antibody expressly includes all classes of immunoglobulin molecules (e.g., IgG, IgE, IgM, IgD, IgA, and IgY), as well as the corresponding subclasses (e.g., $IgG_1$, $IgG_2$, $IgG_3$, $IgG_4$, $IgA_1$, $IgA_2$).

With respect to contemplated antibody fragments it should be noted that fragments will include one or more portions of an antibody that contains CDRs (typically all CDRs of at least one of $V_H$ and $V_L$), and optionally the framework residues. Thus, antibody fragments will in most cases exhibit an ability to specifically bind to the antigen (here: an epitope of TIM3). Among other fragments, especially contemplated fragments include Fab', F(ab')$_2$, Fv, scFv, and mutants thereof, naturally occurring variants, as well as fusion proteins with various non-antibody polypeptides (e.g., toxin, antigen recognition site for a different antigen, enzyme, receptor, receptor ligand, etc.). Viewed from a different perspective, contemplated antibody fragments will have an amino acid sequence of at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

In further contemplated aspects, the antibody of fragment thereof may be used for in vitro or in vivo diagnosis and as such be coupled to a detectable label. For example, suitable detectable labels include various enzymes, fluorescent materials, luminescent materials, bioluminescent materials, radioactive materials, positron emitting metals, and nonradioactive paramagnetic metal ions. The detectable label can be coupled or conjugated either directly to the antibody or indirectly, through an intermediate (e.g., chemical or biological linker) using techniques known in the art. Additionally, or alternatively, contemplated antibodies and fragments thereof may also be coupled to a solid support, which is particularly useful for immunoassays or purification of TIM3 or cells expressing TIM3. For example, suitable supports include magnetic beads, glass, cellulose, polyacrylamide, nylon, polystyrene, polyvinyl chloride, and polypropylene.

Contemplated antibodies and fragments thereof may also be coupled to or comprise a therapeutic agent to target the agent to a cell expressing TIM3. For example, especially contemplated therapeutic agents include chemotherapeutic drugs, radionuclide, and immune stimulants (e.g., cytokine, a cytokine analog, a chemokine, or a checkpoint inhibitor). There are numerous manners of preparing antibody-drug conjugates, and all of these are deemed suitable for use herein.

In especially preferred aspects, contemplated antibodies or fragments thereof may also be prepared as chimeric proteins in which at least one portion of the antibody is continuous with a second polypeptide (optionally via a preferably flexible linker). For example, suitable chimeric proteins may be configured as chimeric antigen receptors (CAR) that may have an intracellular signaling portion, a transmembrane portion, and an extracellular recognition domain. In such case, it is generally contemplated that the recognition domain includes an antibody fragment (e.g., scFv or single domain) and/or that the intracellular signaling domain comprises an activating/ITAM motif. Among other options, contemplated may be first, second, or third generation CARs with a variety of domains known in the art. For example, suitable CARS will include a CD8 hinge portion, a CD28 transmembrane domain, and a CD3zeta (CD3ζ) or Fc receptor epsilon (FcεRIγ) signaling domain. Alternatively, the signaling domain may also include one or more of a CD28 signaling domain, a 4-1BB signaling domain, and a CD3zeta (CD3ζ) signaling domain. Among other options, such chimeric antigen receptors are preferably expressed in cytotoxic immune competent cells, and especially in NK cells and/or T cells.

On the other hand, and especially where the anti-TIM3 antibody or fragment thereof is used to additionally mediate cell or receptor/ligand contact, contemplated chimeric proteins may be constructed as a bispecific fusion protein, as a bispecific killer cell engager (BiKE), or as a trispecific killer cell engager (TriKe). For example, a bispecific fusion protein may comprise the anti-TIM3 antibody or portion thereof and a second affinity ligand that selectively binds to a desired target. Such target may be a soluble protein or a cell-bound protein, and especially contemplated targets include PD-L1. On the other hand, contemplated chimeric molecules may be constructed as bispecific polypeptides (e.g., first scFv coupled via linker to second scFv) in which one portion comprises the anti-TIM3 antibody or portion thereof and in which the other portion has a binder to a marker specific for an immune competent cell (e.g., anti-CD3).

In further contemplated aspects, the anti-TIM3 antibody or portion thereof may also be coupled to an IgG-Fc/IL15Ra/IL15 hybrid (e.g., ALT803). For example, the anti-TIM3 antibody fragment could be a scFv portion that is coupled to one or both arms of the hybrid to so form a T×M (see T×M technology at URL:Altorbioscience.com). Or the anti-TIM3 antibody fragment could be a scFv portion that is coupled to one arm of the hybrid, while the other arm of the hybrid could be a scFv portion that binds PD-L1 (or other immune related ligand).

As should be appreciated, nucleic acids encoding contemplated anti-TIM3 antibodies are also expressly considered herein, and the skilled artisan will be readily able to prepare such nucleic acids (e.g., DNA, RNA) and recombinant entities comprising such nucleic acids. Among other options, suitable recombinant entities include yeast, bacterial, and viral expression vectors, linear DNA for genome editing or other integration, RNA, etc. of course, it should be recognized that the recombinant nucleic acids will include suitable regulatory elements to allow for expression of the recombinant construct. Moreover, it should be noted that the nucleic acid will typically make use of codon-optimization with respect to the host cells that include and express the recombinant nucleic acid.

As will be readily appreciated, use of anti-TIM3 antibodies, fragments thereof, or chimeric proteins containing anti-TIM3 antibodies or fragments thereof is particularly advantageous where immune suppression mediated by TIM3 is to be reduced or inhibited. Consequently, antibodies or portions thereof can be especially useful in the reversal or reduction of immune suppression via TIM3 signaling. Moreover, where cancer cell express and display TIM3, the cells may offer a further therapeutic target (e.g., via targeting with a chimeric molecule that has a TIM3 binding portion and an immune stimulatory portion (e.g., ALT-803)).

In view of these findings, the inventors also contemplate use of various recombinant TIM3 binding molecules such as antibodies and fragments thereof as well as cells expressing anti-TIM3 CAR molecules and pharmaceutical compositions comprising same. Most typically, such recombinant proteins may be soluble forms of antibodies and fragments thereof, soluble chimeric molecules comprising a TIM3 binding portion, or membrane bound molecules such as CAR comprising a TIM3 binding portion. For example, recombinant TIM3 binding CARs may be expressed in a cytotoxic cell such as a T cell, a natural killer cell, or an NKT cell.

It is contemplated that such prepared or generated pharmaceutical composition can be administered to a patient having a tumor to increase effectiveness of immune therapy to so treat the tumor (e.g., to modulate (e.g., reduce, abrogate, etc.) immune suppression by the tumor, to reduce the tumor size, etc.). In some embodiments, pharmaceutical composition and/or the tumor vaccine can be administered via systemic injection including subcutaneous, subdermal injection, or intravenous injection. In other embodiments, where the systemic injection may not be efficient (e.g., for brain tumors, etc.) or more localized treatment is desired, it is contemplated that the recombinant immunoglobulin protein complex and/or pharmaceutical compositions can be administered via intratumoral injection. As used herein, the term "administering" refers to both direct and indirect administration of the compounds and compositions contemplated herein, where direct administration is typically performed by a health care professional (e.g., physician, nurse, etc.), while indirect administration typically includes a step of providing or making the compounds and compositions available to the health care professional for direct administration.

With respect to dose and schedule of the administration, it is contemplated that the dose and/or schedule may vary depending on depending on the type of protein, protein complex, or the type of the pharmaceutical composition (e.g., virus, bacteria, yeast, in combination with recombinant protein complex, etc.), type and prognosis of disease (e.g., tumor type, size, location), health status of the patient (e.g., including age, gender, etc.). While it may vary, the dose and schedule may be selected and regulated such that the formulation does not provide any significant toxic effect to the host normal cells, yet sufficient to be reduce immune suppression by reduced T cell differentiation and/or activation in the tumor microenvironment. Thus, in a preferred embodiment, an optimal or desired condition of administering the formulation can be determined based on a predetermined threshold. For example, the predetermined threshold may be a predetermined local or systemic concentration of T-cell activating, or T-cell released cytokines (e.g., IL-2, IL-12, IFN-$\gamma$, IL-12, IL-23, IL-1b, IL-6, or TGF-$\beta$, etc.) in the tumor microenvironment. Therefore, administration conditions are typically adjusted to have one or more of those cytokines increased in the tumor microenvironment at least 20%, at least 30%, at least 50%, at least 60%, at least 70% at least for 24 hours, 48 hours, 72 hours, 7 days, etc. Moreover, it is contemplated that the compounds and compositions presented herein may be co-administered (contemporaneously or sequentially) with NK cells. For example, suitable NK cells include autologous NK cells as well as NK92 cells and derivatives thereof (e.g., aNK cells, haNK cells, taNK cells, al commercially available from NantKwest, 9920 Jefferson Blvd. Culver City, CA 90232).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

SEQUENCE LISTING

```
Sequence total quantity: 60
SEQ ID NO: 1           moltype = AA  length = 120
FEATURE                Location/Qualifiers
REGION                 1..120
                       note = 64-6 VH amino acid sequence
source                 1..120
                       mol_type = protein
                       organism = synthetic construct
SEQUENCE: 1
EVQLVESGGG LVQPGGSLRL SCAASGFTFS RYAMHWVRQA PGKGLEWVSA ISGSGGYTYY   60
ADSVKGRFTI SRDNSKNTLY LQMNSLRAED TAVYYCARDR HWVLSAFDVW GQGTLVTVSS  120

SEQ ID NO: 2           moltype = AA  length = 107
FEATURE                Location/Qualifiers
REGION                 1..107
                       note = 64-6 VL amino acid sequence
source                 1..107
                       mol_type = protein
                       organism = synthetic construct
SEQUENCE: 2
DIQMTQSPSS LSASVGDRVT ITCQASQDIS NYLNWYQQKP GKAPKLLIYD ASNLETGVPS   60
RFSGSGSGTD FTFTISSLQP EDIATYYCQQ YDTFPFTFGQ GTKVEIK                107

SEQ ID NO: 3           moltype = AA  length = 124
FEATURE                Location/Qualifiers
REGION                 1..124
                       note = 64-15 VH amino acid sequence
source                 1..124
                       mol_type = protein
                       organism = synthetic construct
SEQUENCE: 3
EVQLVESGGG LVQPGGSLRL SCAASGFTFS SYYMHWVRQA PGKGLEWVSG ISGSGGSTYY   60
ADSVKGRFTI SRDNSKNTLY LQMNSLRAED TAVYYCARGR GAWPFTRVVA FDVWGQGTLV  120
TVSS                                                               124

SEQ ID NO: 4           moltype = AA  length = 107
FEATURE                Location/Qualifiers
REGION                 1..107
                       note = 64-15 VL amino acid sequence
source                 1..107
                       mol_type = protein
                       organism = synthetic construct
SEQUENCE: 4
DIQMTQSPSS LSASVGDRVT ITCQASQDIS NYLNWYQQKP GKAPKLLIYD ASNLETGVPS   60
RFSGSGSGTD FTFTISSLQP EDIATYYCQQ WTALPLTFGQ GTKVEIK                107
```

```
SEQ ID NO: 5              moltype = AA   length = 122
FEATURE                   Location/Qualifiers
REGION                    1..122
                          note = 64-31 VH amino acid sequence
source                    1..122
                          mol_type = protein
                          organism = synthetic construct
SEQUENCE: 5
MEVQLVESGG GLVQPGGSLR LSCAASGFTF SAYAMHWVRQ APGKGLEWVS AINGNGGRTY    60
YADSVKGRFT ISRDNSKNTL YLQMNSLRAE DTAVYYCARD LTRTVPFAFD VWGQGTLVTV   120
SS                                                                 122

SEQ ID NO: 6              moltype = AA   length = 107
FEATURE                   Location/Qualifiers
REGION                    1..107
                          note = 64-31 VL amino acid sequence
source                    1..107
                          mol_type = protein
                          organism = synthetic construct
SEQUENCE: 6
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ ATGWPFTFGQ GTKVEIK                 107

SEQ ID NO: 7              moltype = AA   length = 121
FEATURE                   Location/Qualifiers
REGION                    1..121
                          note = 64-32 VH amino acid sequence
source                    1..121
                          mol_type = protein
                          organism = synthetic construct
SEQUENCE: 7
MEVQLVESGG GLVQPGGSLR LSCAASGFTF SKYAMHWVRQ APGKGLEWVS AISGSGGYTY    60
YADSVKGRFT ISRDNSKNTL YLQMNSLRAE DTAVYYCARD LDFRIVGFDV WGQGTLVTVS   120
S                                                                  121

SEQ ID NO: 8              moltype = AA   length = 107
FEATURE                   Location/Qualifiers
REGION                    1..107
                          note = 64-32 VL amino acid sequence
source                    1..107
                          mol_type = protein
                          organism = synthetic construct
SEQUENCE: 8
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ FNTVPLTFGQ GTKVEIK                 107

SEQ ID NO: 9              moltype = AA   length = 121
FEATURE                   Location/Qualifiers
REGION                    1..121
                          note = 64-39 VH amino acid sequence
source                    1..121
                          mol_type = protein
                          organism = synthetic construct
SEQUENCE: 9
MEVQLVESGG GLVQPGGSLR LSCAASGFTF SRYAMHWVRQ APGKGLEWVS GISGSGGGTY    60
YADSVKGRFT ISRDNSKNTL YLQMNSLRAE DTAVYYCARD LDYRVSGFDV WGQGTLVTVS   120
S                                                                  121

SEQ ID NO: 10             moltype = AA   length = 107
FEATURE                   Location/Qualifiers
REGION                    1..107
                          note = 64-39 VL amino acid sequence
source                    1..107
                          mol_type = protein
                          organism = synthetic construct
SEQUENCE: 10
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ FYSVPLTFGQ GTKVEIK                 107

SEQ ID NO: 11             moltype = AA   length = 121
FEATURE                   Location/Qualifiers
REGION                    1..121
                          note = 66-6 VH amino acid sequence
source                    1..121
                          mol_type = protein
                          organism = synthetic construct
SEQUENCE: 11
MEVQLVESGG GLVQPGGSLR LSCAASGFTF SKYAMHWVRQ APGKGLEWVS AISGSGGSTY    60
```

```
YADSVKGRFT ISRDNSKNTL YLQMNSLRAE DTAVYYCARD LDYRFSGFDV WGQGTLVTVS    120
S                                                                  121

SEQ ID NO: 12              moltype = AA  length = 107
FEATURE                    Location/Qualifiers
REGION                     1..107
                           note = 66-6 VL amino acid sequence
source                     1..107
                           mol_type = protein
                           organism = synthetic construct
SEQUENCE: 12
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ FAAIPLTFGQ GTKVEIK                 107

SEQ ID NO: 13              moltype = AA  length = 450
FEATURE                    Location/Qualifiers
REGION                     1..450
                           note = 64-6 HC amino acid sequence
source                     1..450
                           mol_type = protein
                           organism = synthetic construct
SEQUENCE: 13
EVQLVESGGG LVQPGGSLRL SCAASGFTFS RYAMHWVRQA PGKGLEWVSA ISGSGGYTYY    60
ADSVKGRFTI SRDNSKNTLY LQMNSLRAED TAVYYCARDR HWVLSAFDVW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 14              moltype = AA  length = 214
FEATURE                    Location/Qualifiers
REGION                     1..214
                           note = 64-6 LC amino acid sequence
source                     1..214
                           mol_type = protein
                           organism = synthetic construct
SEQUENCE: 14
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ YDTFPFTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 15              moltype = AA  length = 454
FEATURE                    Location/Qualifiers
REGION                     1..454
                           note = 64-15 HC amino acid sequence
source                     1..454
                           mol_type = protein
                           organism = synthetic construct
SEQUENCE: 15
EVQLVESGGG LVQPGGSLRL SCAASGFTFS SYYMHWVRQA PGKGLEWVSG ISGSGGSTYY    60
ADSVKGRFTI SRDNSKNTLY LQMNSLRAED TAVYYCARGR GAWPFTRVVA FDVWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SRDELTKNQV SLTCLVKGFY PSDIAVEWES NGQPENNYKT TPPVLDSDGS FFLYSKLTVD   420
KSRWQQGNVF SCSVMHEALH NHYTQKSLSL SPGK                              454

SEQ ID NO: 16              moltype = AA  length = 214
FEATURE                    Location/Qualifiers
REGION                     1..214
                           note = 64-15 LC amino acid sequence
source                     1..214
                           mol_type = protein
                           organism = synthetic construct
SEQUENCE: 16
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ WTALPLTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 17              moltype = AA  length = 452
FEATURE                    Location/Qualifiers
REGION                     1..452
                           note = 64-31 HC amino acid sequence
source                     1..452
```

```
                      mol_type = protein
                      organism = synthetic construct
SEQUENCE: 17
MEVQLVESGG GLVQPGGSLR LSCAASGFTF SAYAMHWVRQ APGKGLEWVS AINGNGGRTY     60
YADSVKGRFT ISRDNSKNTL YLQMNSLRAE DTAVYYCARD LTRTVPFAFD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 18        moltype = AA  length = 214
FEATURE              Location/Qualifiers
REGION               1..214
                      note = 64-31 LC amino acid sequence
source               1..214
                      mol_type = protein
                      organism = synthetic construct
SEQUENCE: 18
DIQMTQSPSS LSASVGDRVT ITCQASQDIS NYLNWYQQKP GKAPKLLIYD ASNLETGVPS     60
RFSGSGSGTD FTFTISSLQP EDIATYYCQQ ATGWPFTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 19        moltype = AA  length = 451
FEATURE              Location/Qualifiers
REGION               1..451
                      note = 64-32 HC amino acid sequence
source               1..451
                      mol_type = protein
                      organism = synthetic construct
SEQUENCE: 19
MEVQLVESGG GLVQPGGSLR LSCAASGFTF SKYAMHWVRQ APGKGLEWVS AISGSGGYTY     60
YADSVKGRFT ISRDNSKNTL YLQMNSLRAE DTAVYYCARD LDFRIVGFDV WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPELLG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRD    360
ELTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                   451

SEQ ID NO: 20        moltype = AA  length = 214
FEATURE              Location/Qualifiers
REGION               1..214
                      note = 64-32 LC amino acid sequence
source               1..214
                      mol_type = protein
                      organism = synthetic construct
SEQUENCE: 20
DIQMTQSPSS LSASVGDRVT ITCQASQDIS NYLNWYQQKP GKAPKLLIYD ASNLETGVPS     60
RFSGSGSGTD FTFTISSLQP EDIATYYCQQ FNTVPLTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 21        moltype = AA  length = 451
FEATURE              Location/Qualifiers
REGION               1..451
                      note = 64-39 HC amino acid sequence
source               1..451
                      mol_type = protein
                      organism = synthetic construct
SEQUENCE: 21
MEVQLVESGG GLVQPGGSLR LSCAASGFTF SRYAMHWVRQ APGKGLEWVS GISGSGGGTY     60
YADSVKGRFT ISRDNSKNTL YLQMNSLRAE DTAVYYCARD LDYRVSGFDV WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPELLG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRD    360
ELTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                   451

SEQ ID NO: 22        moltype = AA  length = 214
FEATURE              Location/Qualifiers
REGION               1..214
                      note = 64-39 LC amino acid sequence
source               1..214
                      mol_type = protein
                      organism = synthetic construct
```

```
SEQUENCE: 22
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ FYSVPLTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 23           moltype = AA   length = 451
FEATURE                 Location/Qualifiers
REGION                  1..451
                        note = 66-6 HC amino acid sequence
source                  1..451
                        mol_type = protein
                        organism = synthetic construct
SEQUENCE: 23
MEVQLVESGG GLVQPGGSLR LSCAASGFTF SKYAMHWVRQ APGKGLEWVS AISGSGGSTY    60
YADSVKGRFT ISRDNSKNTL YLQMNSLRAE DTAVYYCARD LDYRFSGFDV WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 24           moltype = AA   length = 214
FEATURE                 Location/Qualifiers
REGION                  1..214
                        note = 66-6 LC amino acid sequence
source                  1..214
                        mol_type = protein
                        organism = synthetic construct
SEQUENCE: 24
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ FAAIPLTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 25           moltype = AA   length = 6
FEATURE                 Location/Qualifiers
REGION                  1..6
                        note = 64-6 CDR-H1
source                  1..6
                        mol_type = protein
                        organism = synthetic construct
SEQUENCE: 25
SRYAMH                                                                6

SEQ ID NO: 26           moltype = AA   length = 10
FEATURE                 Location/Qualifiers
REGION                  1..10
                        note = 64-6 CDR-H2
source                  1..10
                        mol_type = protein
                        organism = synthetic construct
SEQUENCE: 26
AISGSGGYTY                                                           10

SEQ ID NO: 27           moltype = AA   length = 11
FEATURE                 Location/Qualifiers
REGION                  1..11
                        note = 64-6 CDR-H3
source                  1..11
                        mol_type = protein
                        organism = synthetic construct
SEQUENCE: 27
DRHWVLSAFD V                                                         11

SEQ ID NO: 28           moltype = AA   length = 11
FEATURE                 Location/Qualifiers
REGION                  1..11
                        note = 64-6 CDR-L1
source                  1..11
                        mol_type = protein
                        organism = synthetic construct
SEQUENCE: 28
QASQDISNYL N                                                         11

SEQ ID NO: 29           moltype = AA   length = 7
FEATURE                 Location/Qualifiers
REGION                  1..7
```

```
                        note = 64-6 CDR-L2
source                  1..7
                        mol_type = protein
                        organism = synthetic construct
SEQUENCE: 29
DASNLET                                                                 7

SEQ ID NO: 30           moltype = AA  length = 9
FEATURE                 Location/Qualifiers
REGION                  1..9
                        note = 64-6 CDR-L3
source                  1..9
                        mol_type = protein
                        organism = synthetic construct
SEQUENCE: 30
QQYDTFPFT                                                               9

SEQ ID NO: 31           moltype = AA  length = 6
FEATURE                 Location/Qualifiers
REGION                  1..6
                        note = 64-15 CDR-H1
source                  1..6
                        mol_type = protein
                        organism = synthetic construct
SEQUENCE: 31
SSYYMH                                                                  6

SEQ ID NO: 32           moltype = AA  length = 10
FEATURE                 Location/Qualifiers
REGION                  1..10
                        note = 64-15 CDR-H2
source                  1..10
                        mol_type = protein
                        organism = synthetic construct
SEQUENCE: 32
GISGSGGSTY                                                              10

SEQ ID NO: 33           moltype = AA  length = 18
FEATURE                 Location/Qualifiers
REGION                  1..18
                        note = 64-15 CDR-H3
source                  1..18
                        mol_type = protein
                        organism = synthetic construct
SEQUENCE: 33
CARGRGAWPF TRVVAFDV                                                     18

SEQ ID NO: 34           moltype = AA  length = 11
FEATURE                 Location/Qualifiers
REGION                  1..11
                        note = 64-15 CDR-L1
source                  1..11
                        mol_type = protein
                        organism = synthetic construct
SEQUENCE: 34
QASQDISNYL N                                                            11

SEQ ID NO: 35           moltype = AA  length = 7
FEATURE                 Location/Qualifiers
REGION                  1..7
                        note = 64-15 CDR-L2
source                  1..7
                        mol_type = protein
                        organism = synthetic construct
SEQUENCE: 35
DASNLET                                                                 7

SEQ ID NO: 36           moltype = AA  length = 9
FEATURE                 Location/Qualifiers
REGION                  1..9
                        note = 64-15 CDR-L3
source                  1..9
                        mol_type = protein
                        organism = synthetic construct
SEQUENCE: 36
QQWTALPLT                                                               9

SEQ ID NO: 37           moltype = AA  length = 6
FEATURE                 Location/Qualifiers
```

```
REGION                    1..6
                          note = 64-31 CDR-H1
source                    1..6
                          mol_type = protein
                          organism = synthetic construct
SEQUENCE: 37
SAYAMH                                                                          6

SEQ ID NO: 38             moltype = AA   length = 10
FEATURE                   Location/Qualifiers
REGION                    1..10
                          note = 64-31 CDR-H2
source                    1..10
                          mol_type = protein
                          organism = synthetic construct
SEQUENCE: 38
AINGNGGRTY                                                                     10

SEQ ID NO: 39             moltype = AA   length = 12
FEATURE                   Location/Qualifiers
REGION                    1..12
                          note = 64-31 CDR-H3
source                    1..12
                          mol_type = protein
                          organism = synthetic construct
SEQUENCE: 39
DLTRTVPFAF DV                                                                  12

SEQ ID NO: 40             moltype = AA   length = 11
FEATURE                   Location/Qualifiers
REGION                    1..11
                          note = 64-31 CDR-L1
source                    1..11
                          mol_type = protein
                          organism = synthetic construct
SEQUENCE: 40
QASQDISNYL N                                                                   11

SEQ ID NO: 41             moltype = AA   length = 7
FEATURE                   Location/Qualifiers
REGION                    1..7
                          note = 64-31 CDR-L2
source                    1..7
                          mol_type = protein
                          organism = synthetic construct
SEQUENCE: 41
DASNLET                                                                         7

SEQ ID NO: 42             moltype = AA   length = 9
FEATURE                   Location/Qualifiers
REGION                    1..9
                          note = 64-31 CDR-L3
source                    1..9
                          mol_type = protein
                          organism = synthetic construct
SEQUENCE: 42
QQATGWPFT                                                                       9

SEQ ID NO: 43             moltype = AA   length = 6
FEATURE                   Location/Qualifiers
REGION                    1..6
                          note = 64-32 CDR-H1
source                    1..6
                          mol_type = protein
                          organism = synthetic construct
SEQUENCE: 43
SKYAMH                                                                          6

SEQ ID NO: 44             moltype = AA   length = 10
FEATURE                   Location/Qualifiers
REGION                    1..10
                          note = 64-32 CDR-H2
source                    1..10
                          mol_type = protein
                          organism = synthetic construct
SEQUENCE: 44
AISGSGGYTY                                                                     10

SEQ ID NO: 45             moltype = AA   length = 11
```

```
FEATURE             Location/Qualifiers
REGION              1..11
                    note = 64-32 CDR-H3
source              1..11
                    mol_type = protein
                    organism = synthetic construct
SEQUENCE: 45
DLDFRIVGFD V                                                                    11

SEQ ID NO: 46       moltype = AA  length = 11
FEATURE             Location/Qualifiers
REGION              1..11
                    note = 64-32 CDR-L1
source              1..11
                    mol_type = protein
                    organism = synthetic construct
SEQUENCE: 46
QASQDISNYL N                                                                    11

SEQ ID NO: 47       moltype = AA  length = 7
FEATURE             Location/Qualifiers
REGION              1..7
                    note = 64-32 CDR-L2
source              1..7
                    mol_type = protein
                    organism = synthetic construct
SEQUENCE: 47
DASNLET                                                                          7

SEQ ID NO: 48       moltype = AA  length = 9
FEATURE             Location/Qualifiers
REGION              1..9
                    note = 64-32 CDR-L3
source              1..9
                    mol_type = protein
                    organism = synthetic construct
SEQUENCE: 48
QQFNTVPLT                                                                        9

SEQ ID NO: 49       moltype = AA  length = 6
FEATURE             Location/Qualifiers
REGION              1..6
                    note = 64-39 CDR-H1
source              1..6
                    mol_type = protein
                    organism = synthetic construct
SEQUENCE: 49
SRYAMH                                                                           6

SEQ ID NO: 50       moltype = AA  length = 10
FEATURE             Location/Qualifiers
REGION              1..10
                    note = 64-39 CDR-H2
source              1..10
                    mol_type = protein
                    organism = synthetic construct
SEQUENCE: 50
GISGSGGGTY                                                                      10

SEQ ID NO: 51       moltype = AA  length = 11
FEATURE             Location/Qualifiers
REGION              1..11
                    note = 64-39 CDR-H3
source              1..11
                    mol_type = protein
                    organism = synthetic construct
SEQUENCE: 51
DLDYRVSGFD V                                                                    11

SEQ ID NO: 52       moltype = AA  length = 11
FEATURE             Location/Qualifiers
REGION              1..11
                    note = 64-39 CDR-L1
source              1..11
                    mol_type = protein
                    organism = synthetic construct
SEQUENCE: 52
QASQDISNYL N                                                                    11
```

```
SEQ ID NO: 53           moltype = AA  length = 7
FEATURE                 Location/Qualifiers
REGION                  1..7
                        note = 64-39 CDR-L2
source                  1..7
                        mol_type = protein
                        organism = synthetic construct
SEQUENCE: 53
DASNLET                                                                   7

SEQ ID NO: 54           moltype = AA  length = 9
FEATURE                 Location/Qualifiers
REGION                  1..9
                        note = 64-39 CDR-L3
source                  1..9
                        mol_type = protein
                        organism = synthetic construct
SEQUENCE: 54
QQFYSVPLT                                                                 9

SEQ ID NO: 55           moltype = AA  length = 6
FEATURE                 Location/Qualifiers
REGION                  1..6
                        note = 66-6 CDR-H1
source                  1..6
                        mol_type = protein
                        organism = synthetic construct
SEQUENCE: 55
SKYAMH                                                                    6

SEQ ID NO: 56           moltype = AA  length = 10
FEATURE                 Location/Qualifiers
REGION                  1..10
                        note = 66-6 CDR-H2
source                  1..10
                        mol_type = protein
                        organism = synthetic construct
SEQUENCE: 56
AISGSGGSTY                                                               10

SEQ ID NO: 57           moltype = AA  length = 11
FEATURE                 Location/Qualifiers
REGION                  1..11
                        note = 66-6 CDR-H3
source                  1..11
                        mol_type = protein
                        organism = synthetic construct
SEQUENCE: 57
DLDYRFSGFD V                                                             11

SEQ ID NO: 58           moltype = AA  length = 11
FEATURE                 Location/Qualifiers
REGION                  1..11
                        note = 66-6 CDR-L1
source                  1..11
                        mol_type = protein
                        organism = synthetic construct
SEQUENCE: 58
QASQDISNYL N                                                             11

SEQ ID NO: 59           moltype = AA  length = 7
FEATURE                 Location/Qualifiers
REGION                  1..7
                        note = 66-6 CDR-L2
source                  1..7
                        mol_type = protein
                        organism = synthetic construct
SEQUENCE: 59
DASNLET                                                                   7

SEQ ID NO: 60           moltype = AA  length = 9
FEATURE                 Location/Qualifiers
REGION                  1..9
                        note = 66-6 CDR-L3
```

```
source          1..9
                mol_type = protein
                organism = synthetic construct
SEQUENCE: 60
QQFAAIPLT                                                           9
```

What is claimed is:

1. A method of treatment of cancer in an individual in need thereof, the method comprising administering to the individual a pharmaceutical composition comprising an isolated antibody or fragment thereof, wherein the antibody or fragment thereof binds to T-cell immunoglobulin mucin receptor 3 (TIM3), the antibody or fragment thereof comprising:
    a variable heavy chain (VH) domain and a variable light chain (VL) domain;
    wherein the VH domain is selected form the group consisting of SEQ ID NO: 1, SEQ ID NO:3, SEQ ID NO:5, SEQ ID NO:7, SEQ ID NO:9, and SEQ ID NO: 11; and
    wherein the VL domain is selected form the group consisting of SEQ ID NO:2, SEQ ID NO:4, SEQ ID NO:6, SEQ ID NO:8, SEQ ID NO: 10, and SEQ ID NO: 12.

2. The method of claim 1, wherein the antibody or fragment comprises $VH_{64-6}$(SEQ ID NO: 1) and $VL_{64-6}$ (SEQ ID NO:2), wherein the fragment is optionally coupled together by a linker to form an scFv.

3. The method of claim 1, wherein the antibody or fragment comprises $VH_{64-15}$ (SEQ ID NO:3) and $VL_{64-15}$ (SEQ ID NO:4), wherein the fragment is optionally coupled together by a linker to form an scFv.

4. The method of claim 1, wherein the antibody or fragment comprises $VH_{64-31}$ (SEQ ID NO:5) and $VL_{64-31}$ (SEQ ID NO:6), wherein the fragment is optionally coupled together by a linker to form an scFv.

5. The method of claim 1, wherein the antibody or fragment comprises $VH_{64-32}$ (SEQ ID NO:7) and $VL_{64-32}$ (SEQ ID NO:8), wherein the fragment is optionally coupled together by a linker to form an scFv.

6. The method of claim 1, wherein the antibody or fragment comprises $VH_{64-39}$ (SEQ ID NO:9) and $VL_{64-39}$ (SEQ ID NO: 10), wherein the fragment is optionally coupled together by a linker to form an scFv.

7. The method of claim 1, wherein the antibody or fragment comprises $VH_{64-6}$ (SEQ ID NO: 11) and $VL_{64-6}$ (SEQ ID NO: 12), wherein the fragment is optionally coupled together by a linker to form an scFv.

8. The method of claim 1, further comprising administering a therapeutic agent or a detectable label coupled to the antibody or fragment.

9. The method of claim 8, wherein the therapeutic agent is a chemotherapeutic drug, a radionuclide, or an immune stimulant selected from the group consisting of a cytokine, a cytokine analog, a chemokine, or a checkpoint inhibitor.

10. The method of claim 1, comprising administering to the individual a pharmaceutical composition comprising a chimeric protein comprising the antibody or fragment thereof.

11. The method of claim 10 wherein the chimeric protein is a chimeric antigen receptor (CAR) or a bispecific fusion protein.

12. The method of claim 11 wherein the CAR has a CD3zeta (CD3ζ) or Fc receptor epsilon (FcεRIγ) signaling domain.

13. The method of claim 11 wherein the CAR has at least one of a CD28 signaling domain, a 4-1BB signaling domain, and a CD3zeta (CD3ζ) signaling domain.

14. The method of claim 11 wherein the CAR has a CD8 hinge domain and a CD28 transmembrane domain.

15. The method of claim 11 wherein the CAR is a recombinant CAR expressed on the surface of an NK cell or a cytotoxic T cell, and wherein the NK or T cells are administered to the individual.

16. The method of claim 11 wherein the bispecific fusion protein comprises at least one of an IgG Fc portion, an IL15α receptor portion, an IL15 portion, and an IL15 superagonist portion.

17. The method of claim 1, wherein the pharmaceutical composition is administered via systemic injection including subcutaneous, subdermal injection, or intravenous injection.

18. The method of claim 1, wherein the pharmaceutical composition is administered via intratumoral injection.

19. The method of claim 1, further comprising administering NK cells to the individual.

* * * * *